Figure 1:
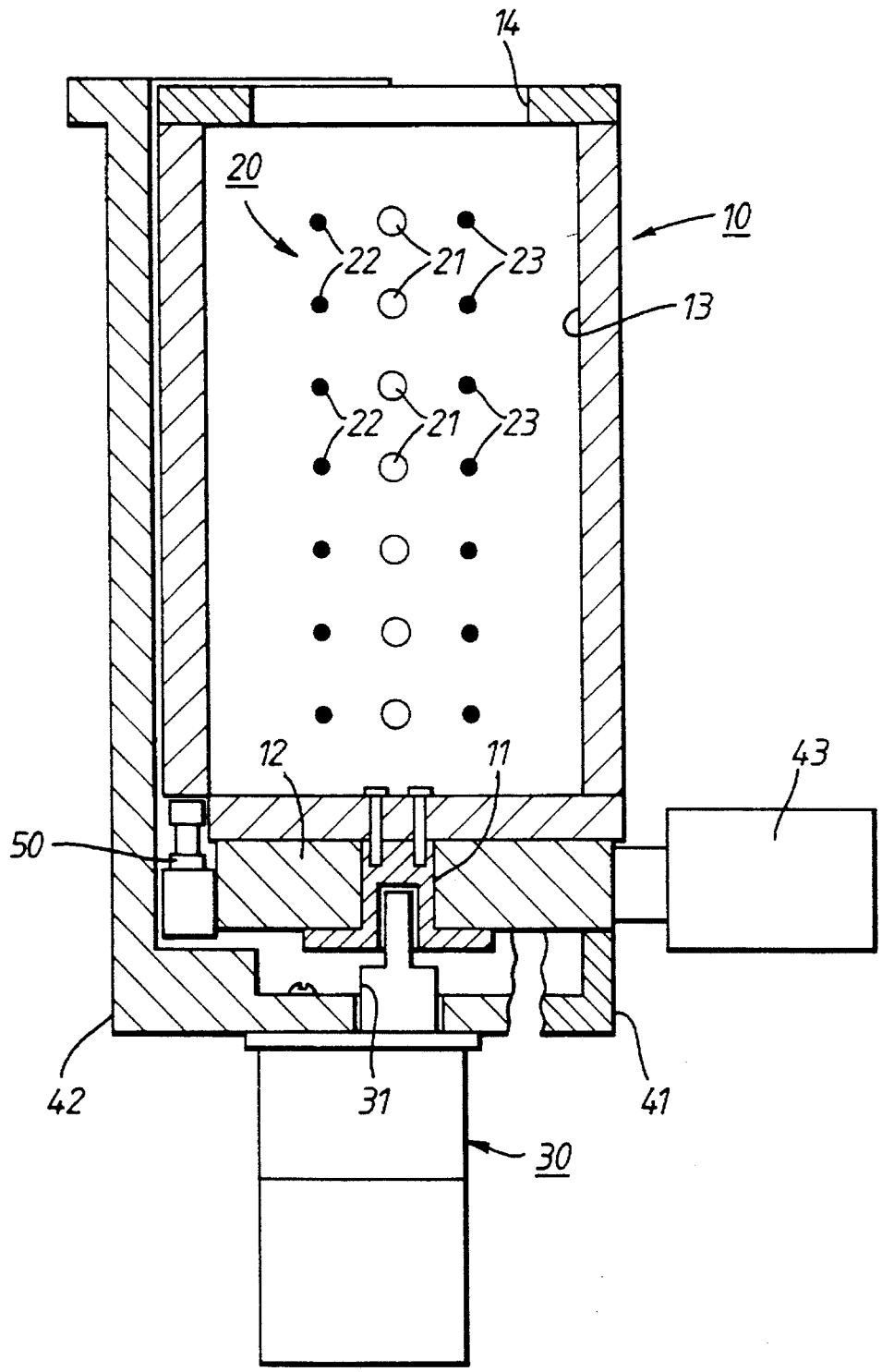

United States Patent [19]
Khodabandehloo et al.

[11] Patent Number: 5,474,023
[45] Date of Patent: Dec. 12, 1995

[54] TEAT INSPECTION

[75] Inventors: Koorosh Khodabandehloo, Bishopston; Toby T. F. Mottram, Chard; Andrew J. Douglas, Windermere, all of England

[73] Assignee: British Technology Group Ltd., London, United Kingdom

[21] Appl. No.: 140,150

[22] PCT Filed: May 1, 1992

[86] PCT No.: PCT/GB92/00799

§ 371 Date: Apr. 13, 1994

§ 102(e) Date: Apr. 13, 1994

[87] PCT Pub. No.: WO92/19098

PCT Pub. Date: Nov. 12, 1992

[30] Foreign Application Priority Data

May 3, 1991 [GB] United Kingdom ............... 9019686

[51] Int. Cl.[6] ........................................ A01J 5/00
[52] U.S. Cl. ........................................ 119/14.1; 119/14.14
[58] Field of Search .................. 119/14.01, 14.1, 119/14.14, 14.18; 250/358.1, 363.08; 128/664, 665

[56] References Cited

U.S. PATENT DOCUMENTS

| 4,134,015 | 1/1979 | Cunningham | 250/358.1 X |
|---|---|---|---|
| 4,386,707 | 6/1983 | Stube | 250/358.1 X |
| 4,596,953 | 6/1986 | Nagasaka et al. | 324/242 |
| 4,726,322 | 2/1988 | Torsius | 119/14.14 |

FOREIGN PATENT DOCUMENTS

| 99757 | 2/1984 | European Pat. Off. . | |
| 207572 | 1/1987 | European Pat. Off. . | |
| 213660 | 3/1987 | European Pat. Off. . | |
| 329248 | 8/1989 | European Pat. Off. | 119/14.14 |
| 2157930 | 10/1985 | United Kingdom . | |
| 2226941 | 7/1990 | United Kingdom . | |
| 2068537 | 8/1991 | United Kingdom . | |
| 8902574 | 3/1989 | WIPO . | |

OTHER PUBLICATIONS

World Patent Index Latest, Week 8544, AN 85-271934.
Patent Abstracts of Japan, vol. 12, No. 51, (P-667) 16 Feb. 1988.
Pig International, vol. 18, No. 2, Feb. 1988, pp. 14-16, 'Slaughterers help with AI costs'.

*Primary Examiner*—Robert P. Swiatek
*Attorney, Agent, or Firm*—Cushman, Darby & Cushman

[57] ABSTRACT

An inspection arrangement for a teat of a milk producing animal, including an elongate probe, at least one radiation sensor on the inner surface of the probe and structure to rotate the probe around a teat, positioned for inspection, to scan the surface of the teat to provide signal output from the at least one sensor, the output indicating a surface condition of the teat, which may be cleanliness and health thereof.

12 Claims, 5 Drawing Sheets

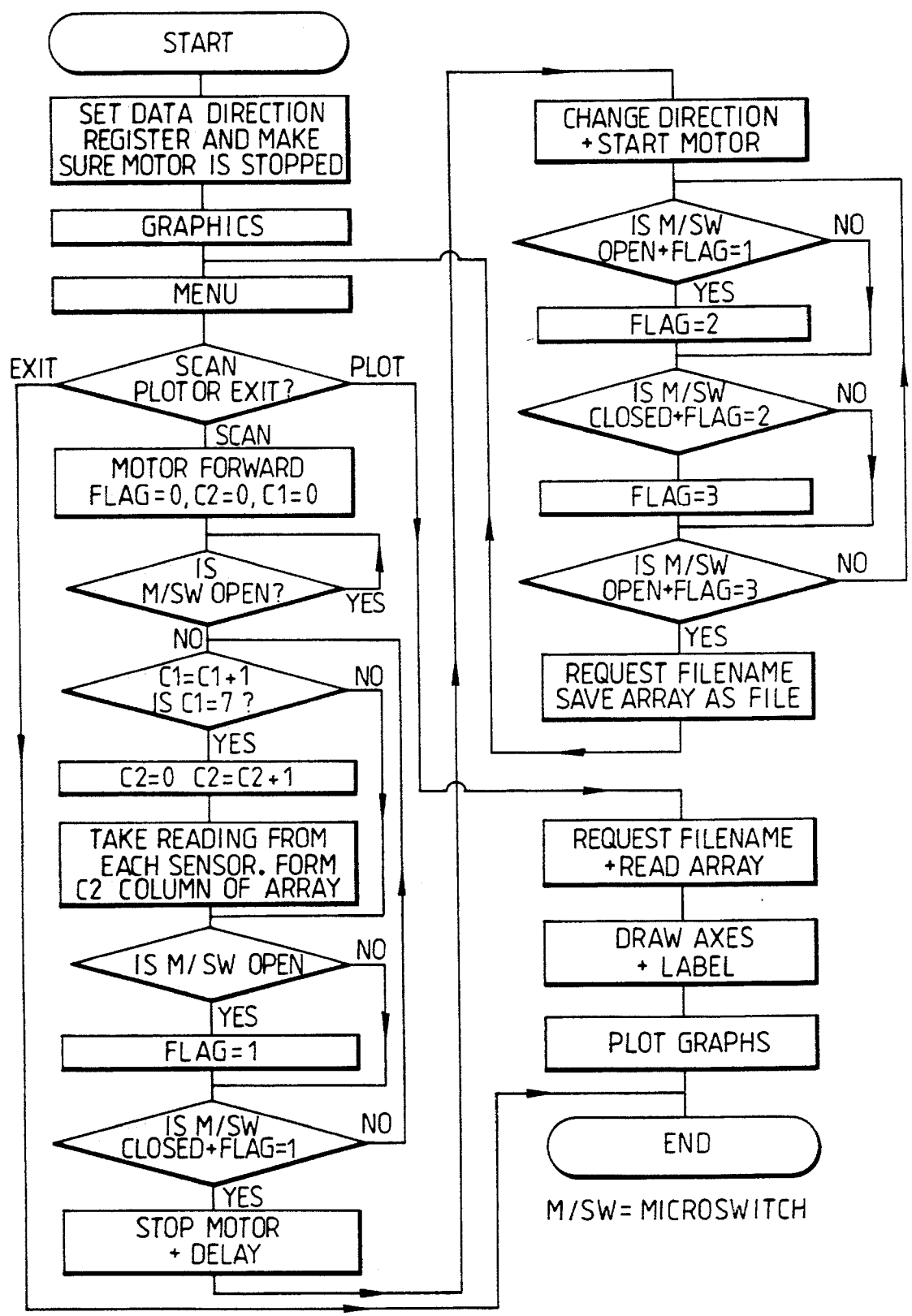
Fig. 6. APPENDIX: BBC PROGRAM FLOW CHART
M/SW = MICROSWITCH 5,474,023

TEAT INSPECTION

The teats and udder of milk animals, such as cows, goats and sheep, are very vulnerable to injury and disease and to becoming soiled. In hand milking and hand-applied machine milking regimes the operator is able to inspect the teats and udder. In particular the teats are inspected to ensure that they are clean, to avoid dirt in the milk, and free from apparent injury or disease which could contaminate the milk from the animal and, if mixed in a bulk supply, that from a whole herd.

In milking regime with automatic application of the milking apparatus, e.g. GB-A 2226941, operator inspection would increase costs by destroying the "unattended" capacity of such regimes. Accordingly there is a need for an inspection technique to ensure that dirt, infection or injury of a teat is identified before milking or before milk from an individual teat is mixed with a bulk supply. Such inspection techniques would also be of value for milking regimes involving operator intervention.

It is an object of the invention to provide an inspection technique for a generally tubular object, typically but not exclusively a teat of a milk animal. The technique is particularly suitable for an automatic procedure, typically but not exclusively an automatically-applied machine milking regime.

According to the invention there is provided an inspection arrangement for a generally tubular object including an elongate probe, at least one radiation sensor on the inner surface of the probe and means to move relatively the probe around a said object positioned for inspection to scan the surface of the object to provide signal output from the at least one sensor, the output indicating a surface condition of the object.

According to one aspect of the invention there is provided an inspection arrangement for a teat of a milk animal in which said probe is a teat-surrounding housing and including at least one radiation detection device in the housing to respond to radiation from a teat therein, which radiation is at least one of reflected and emitted by the teat, and to produce an output signal indicative of said response to said radiation together with means to respond to said output signal to provide an indication that a teat inspected in the arrangement is acceptable or otherwise for milking.

Conveniently the housing is hollow.

Conveniently the housing includes a plurality of detection devices and associated radiation emissive devices and the housing is of generally tubular form to receive a teat and to turn to sweep the surface of the teat with the detection devices.

The detection devices, and radiative devices if present, may be arranged spaced along the length of the tube in a straight line parallel to the axis or in a curve around the inside. The tube may be movable lengthwise as well as being turnable so that several sweeps in turn at lengthwise displaced tube positions can be made. In this way a few devices can be used to build up a detailed scan image from the output signals of the several, displaced, sweeps.

The arrangement may include rotary drive means, such as a d.c. motor, for the turning of the tube together with suitable index means for control of the motor. The lengthwise movement of the tube may be by a linear drive means, such as a rack and pinion, or linked to the rotary drive means to provide a lengthwise shift on each complete turn. The lengthwise movement may be provided by movement of a support for the arrangement such as an automatic milking apparatus described in the above-mentioned GB-A 2226941.

The indication of teat condition may be a simple "GO/NO GO" signal or a display on a VDU based on an assembly of information derived from the sweeps of the teat surface. This display may, if the detection device output can yield the information, indicate that specific problems, e.g. injury or soiling, are present.

The arrangement may be positioned for collection by an automatic milking arrangement and application to a teat before an attempt is made to apply a teat cup for milking.

According to another aspect of the invention there is provided an inspection arrangement for generally tubular objects including radiation emitters and sensors on the inner surface of an elongate probe and means to move relatively the probe around an object positioned for inspection to scan the surface of the object to provide signal outputs from the sensors of surface reflectivity indicating surface conditions of the object.

The probe may a rod or like elongate element.

Figure 2:
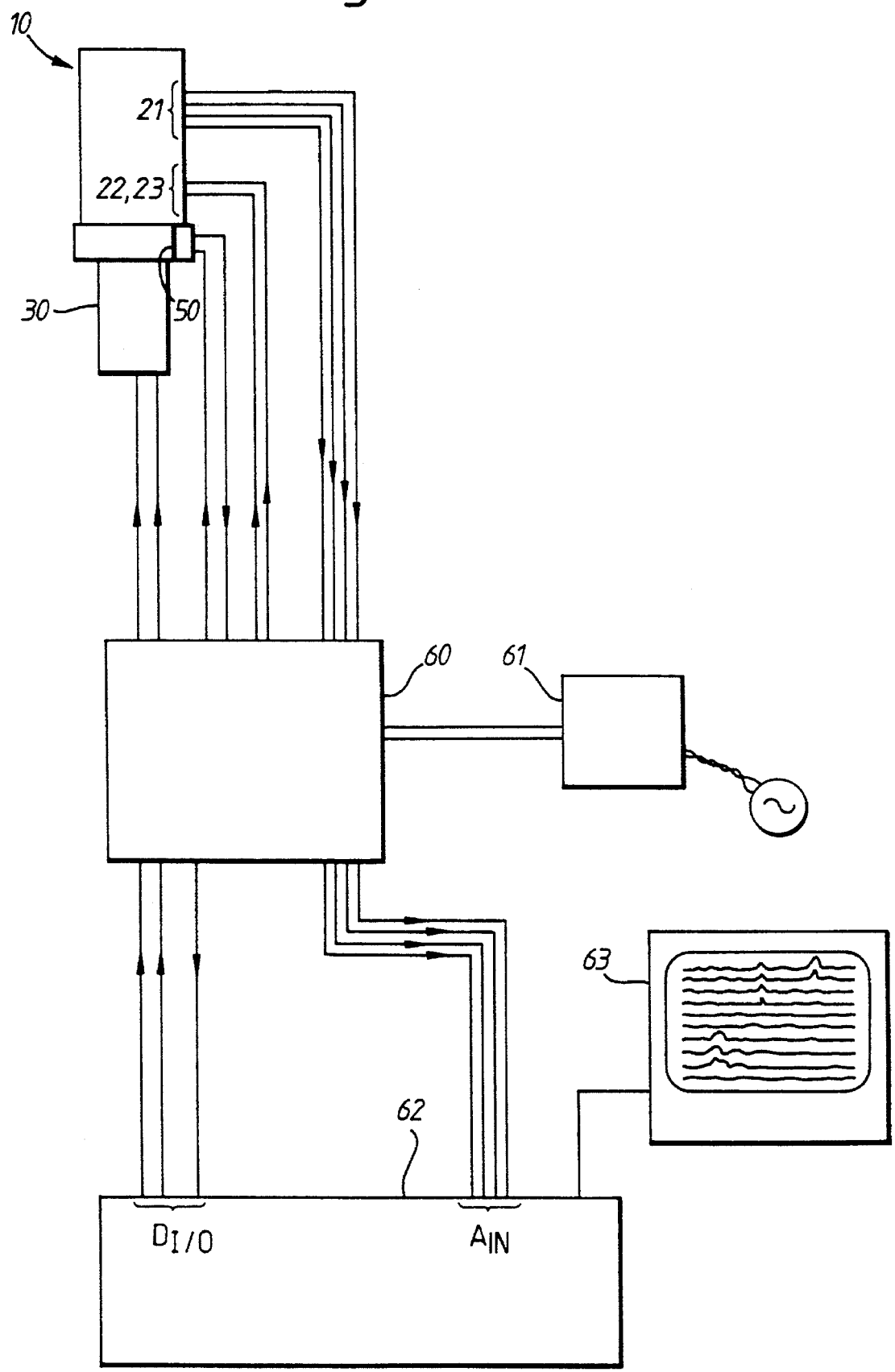
Figure 3:
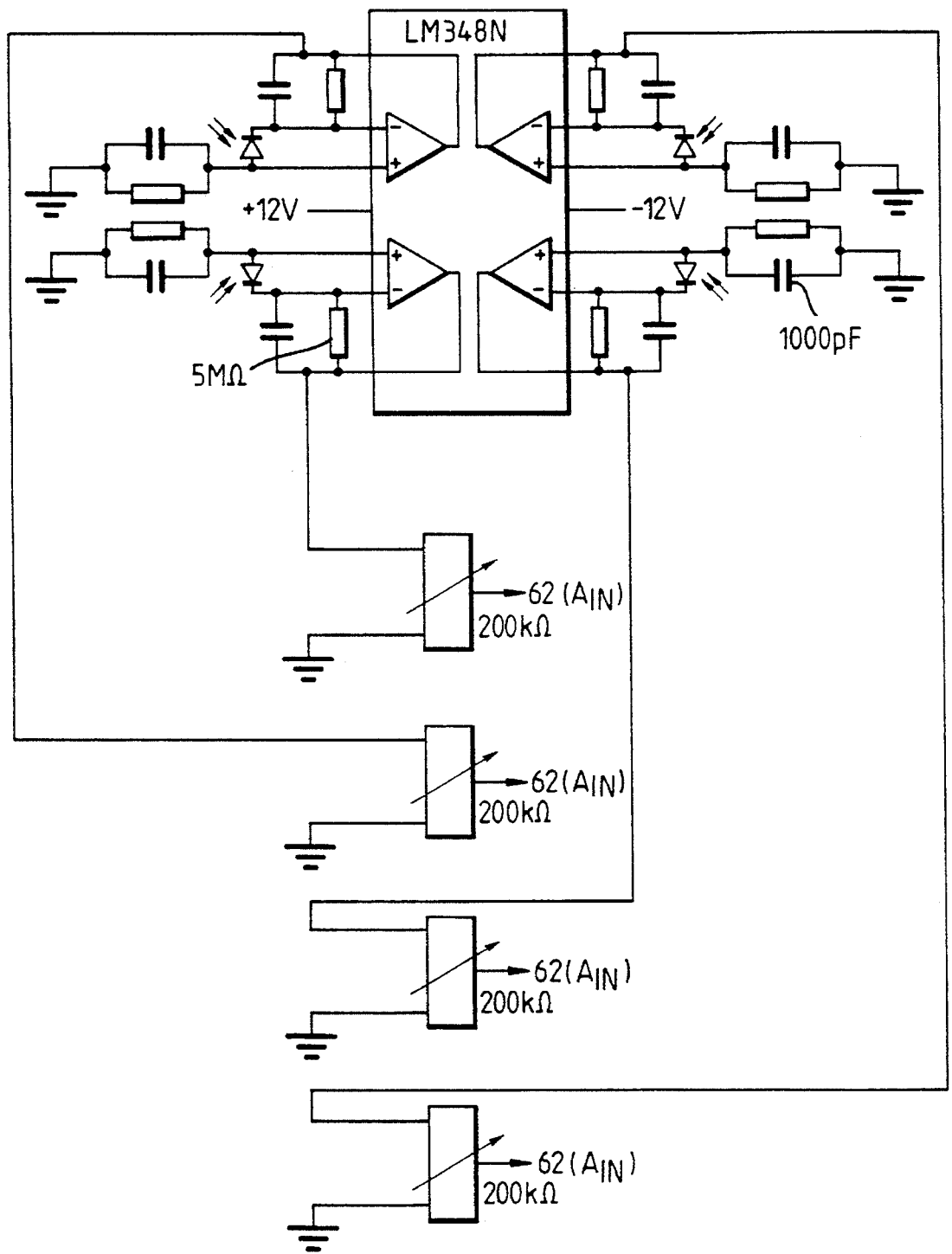
Figure 4:
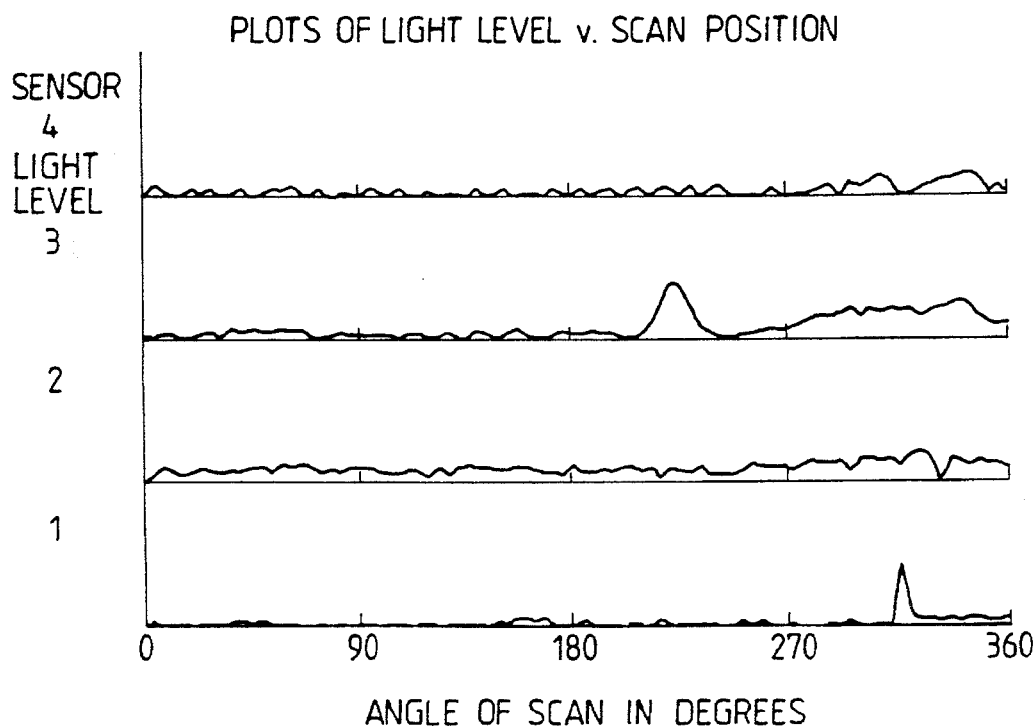
Figure 5:
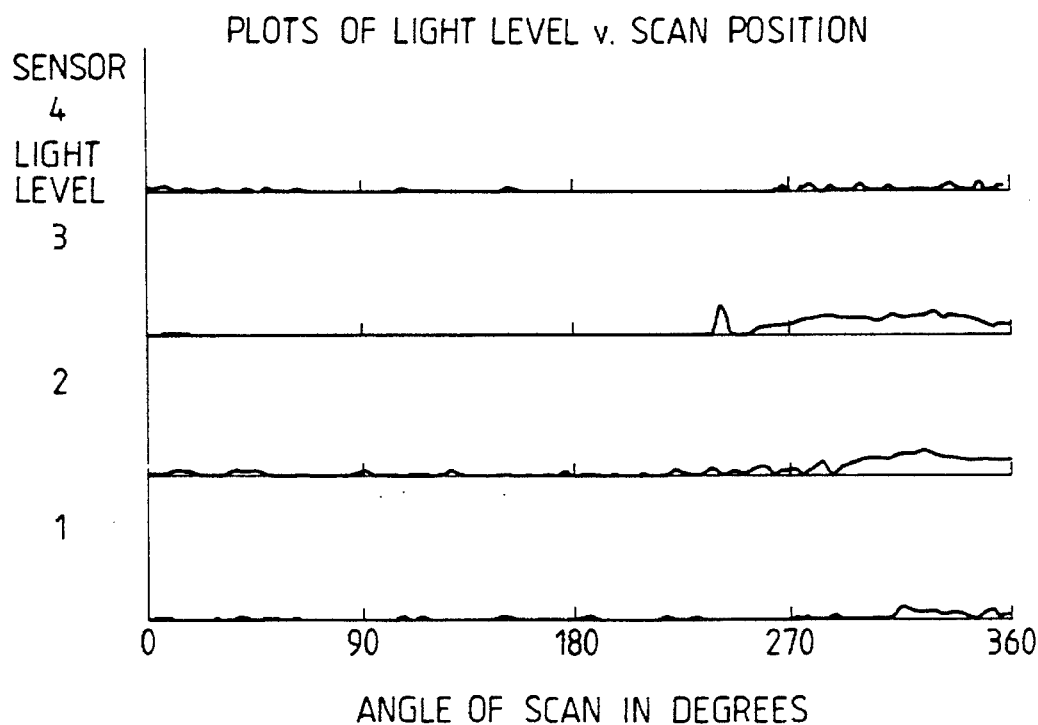

Embodiments of the invention will now be described with reference to the accompanying drawings in which:

FIG. 1 is a cross-section through a sensor part of an arrangement according to the invention, FIG. 2 is a schematic diagram showing how the sensor of FIG. 1 is linked into an arrangement according to the invention, FIG. 3 is a circuit diagram of sensor circuits used in the arrangement of FIGS. 1 and 2, FIGS. 4 and 5 are representations of the indication provided by an embodiment of the invention when in the form displayed on a VDU and FIG. 6 is a flow chart useful in understanding the operation of the invention.

FIG. 1 shows a part-sectional view of the scanner portion of the arrangement. A probe, in this embodiment in the form of a housing of a generally tubular body 10, is attached by adaptor/connector 11 to the output shaft 31 of a slow speed d.c. motor 30. The adaptor/connector 11 revolves freely in a baseplate 12 by which the scanner can be supported. Alternative support forms are shown at 41 and 42. Support 41 is suitable for attachment, at 43, to a conventional robot, such as a PUMA (RTM), not shown. Support 42 is a sleeve around the tube and can be handled in somewhat similar manner to a teat cup by an automatic milking arrangement, such as that described in GB-A 2226941, incorporated herein by reference. Body 10 is open at 14 to allow a teat to enter.

The motor 30 and baseplate 12 are attached to whichever support is used.

A microswitch 50 is attached to plate 12 and a series of teeth (not shown) on the lower part of body 10 interact with the switch to give body position information for control of motor 30, as described below.

An array 20, of radiation emission devices 22, 23 and radiation detection devices 21, is positioned on the inner surface 13 of body 10 along a line parallel to the axis of rotation of body 10 by motor 30. Connections (see FIG. 2) are provided for radiative devices 22, 23, detection devices 21, motor 30 and switch 50. These connections must permit rotation of body 10 but this may be limited as described below to permit relatively simple flexible connections. Radiation emissive devices 22, 23 are connected in parallel and are simultaneously and equally energised. Detection devices 21 are individually connected to provide respective output signals.

The detection devices in one embodiment are Radiospares (RTM) general purpose photodiodes 305–462, which are sensitive to green light, and the emission devices low current LED's. The exact value of light wavelength used can be varied to suit operating conditions. For example moisture on the teats is probably most easily detected at some 4 to 5 micrometers wavelengths, but soiling and injury may be best detected at other wavelengths. It may be convenient to use two wavelengths as well as higher power devices to aid detection of all conditions of interest. In some cases it may be enough to provide the detectors and rely on ambient light or, possibly, infra red radiation emitted from the teat itself, as the source of radiation.

If ambient light conditions, or the intensity and sensitivity of the emitter and detector devices, permit then the probe need not be a housing of a complete tube but a skeletal form, even a single rod to carry the devices.

The spacing and number of detection devices and the speed of rotation depend on the resolution and speed required. For a typical teat, some 75 to 100 millimeters by 15 to 2 millimeters, about 100 points are adequate and some thirty seconds can be allowed for scanning. To receive the teat the tube 10 is some 50 millimeters overall diameter and 100 millimeters long. The aperture 14 is made to fit fairly close to the teat to reduce ambient light entry. The inside of the tube is matt black to reduce reflection.

It will be seen that one turn of the tube will produce seven output signals, each of analogue form and representing a narrow strip around the teat spaced from the others. By moving the tube down a fraction of the detection device spacing several times further strips filling in the gaps are produced.

The devices may be on a curve over the inside of the tube. This can produce closer spacing of scans and better resolution.

FIG. 2 shows a schematic circuit arrangement of the links between the scanner portion and the signal processing and display portions. A circuit board 60, energised by a power supply 61, provides supplies for the radiation emissive devices 22, 23 and controls for the degree of energisation of these devices. The board also provides (FIG. 3) signal conditioning, such as amplification and shaping, for the outputs of detection devices 21 to be connected to the analogue inputs $A_{IN}$ of a microprocessor 62. Motor control circuits for the interface $D_{I/O}$ with the microprocessor 62 are also on board 60.

The motor control is effected by the microswitch 50 and the teeth mentioned above. The motor can be started when the microswitch indicates, by interaction with the teeth mentioned above, that the motor is in the "home" position and drive continues until the motor is again "home". The drive direction is reversed each time to avoid straining the connection wires. Relays are used to respond to the "signal" outputs of the microprocessor 62 to provide the power needed for the motor.

FIG. 6 shows a flow chart giving the overall operational sequences.

The analogue outputs from the detection devices 21 are processed In the microprocessor 62 to produce an indication of teat condition. By way of example this is a display on VDU 63, FIGS. 4 and 5, and represents the scan information and indicates teat conditions by deviations of the scan pattern. Specifically these are for a "test piece" in the form of an elongate object with a marking to mimic a teat with dirt or an injury.

Alternatively the analogue outputs can be processed to give simple GO/NOGO outputs or other required forms.

The exact form of the scanner portion of an inspection arrangement according to the invention depends on the application. Various exemplary forms are set out above but these are not limliting. In the harsh environment of milking the scanner portion must be rugged and proof against liquid contact or entry. The scanner portion can be made more compact by arranging the motor alongside the tube. Appropriate materials and detailed design features will be readily apparent to those skilled in the art.

The techniques described above provide an inspection arrangement which, while particularly appropriate for teat inspection in an automatic milking regime, is suitable for inspection generally, including use other than in agriculture. Use for teat inspection can, of course, be independent of an immediately-following automatic teat cup application being usable as part of a milking regime using hand application of teat cups or as a separate inspection action.

We claim:

1. An inspection arrangement for a teat of a milk producing animal comprising an elongate probe including a teat aperture, the teat aperture being constructed and arranged to receive a teat therein, positioned for inspection, at least one radiation sensor on the inner surface of the probe; and means for rotating the probe with respect to a respective said teat positioned for inspection to scan a peripheral surface of the teat and for providing signal output from the at least one sensor, the output indicating a surface condition of the teat.

2. An inspection arrangement according to claim 1 in which said probe is a teat-surrounding housing, and including at least one radiation detection device in the housing to respond to radiation from a teat therein, which radiation is at least one of reflected and emitted by the teat, and to produce an output signal indicative of said response to said radiation together with means for responding to said output signal to provide an indication that a teat inspected in the arrangement is acceptable for milking.

3. An inspection arrangement according to claim 2 in which the housing includes a plurality of said detection devices and associated radiation emission devices and the housing is generally in the form of a tube to receive a teat and to be turnable to sweep the surface of the teat with the detection devices.

4. An inspection arrangement according to claim 3 in which the detection devices, and radiative devices are arranged spaced along the longitudinal length of a tube in a straight line parallel to the axis or in a curve around the inside.

5. An inspection arrangement according to claim 3 or claim 4 which the tube is movable lengthwise as well as being turnable so that several sweeps in turn at lengthwise displaced tube positions can be made, whereby a number of devices fewer than to cover fully the teat are used to build up a detailed scan image from the output signals of the several, displaced, sweeps.

6. An inspection arrangement according to claim 5 in which the lengthwise movement may be provided by movement of a support for the arrangement.

7. An inspection arrangement according to claim 3 further including rotary drive means for the turning of the tube together with index means for controlling the drive means.

8. An inspection arrangement according to claim 7, in which the tube is movable lengthwise by one of a linear drive means and a rotary drive means.

9. An inspection arrangement according to claim 7 in which the rotary drive means in a d.c. motor.

10. An inspection arrangement according to claim 3 in which the indication of teat condition is one of a simple "GO/NO GO" signal and a visual display based on information derived from the sweeps of the teat surface.

11. An inspection arrangement according to claim 10 in which the display, in response to the detection device output, indicates that at least one of injury and soiling is present.

12. An inspection arrangement according to claim 1 including at least one radiation emitter on said inner surface of the probe and having a signal output including indication of surface reflectivity of the object.

* * * * *